United States Patent [19]

Itagaki et al.

[11] Patent Number: 5,698,185
[45] Date of Patent: Dec. 16, 1997

[54] WHITENING COSMETIC PREPARATION AND METHOD OF USING SAME

[75] Inventors: Yasuharu Itagaki; Hidetoshi Ishikawa; Seiji Kurosawa, all of Sapporo, Japan

[73] Assignee: Snow Brand Milk Products Co., Ltd., Hokkaido, Japan

[21] Appl. No.: 231,190

[22] Filed: Apr. 22, 1994

[30] Foreign Application Priority Data

Apr. 28, 1993 [JP] Japan ................................. 5-124998

[51] Int. Cl.$^6$ ................................................. A61K 7/48
[52] U.S. Cl. ................................. 424/62; 424/401
[58] Field of Search ............................. 424/62, 535, 401

[56] References Cited

U.S. PATENT DOCUMENTS

| | | | |
|---|---|---|---|
| 4,369,174 | 1/1983 | Nagai et al. | 424/62 |
| 4,696,813 | 9/1987 | Higa | 424/62 |
| 4,808,402 | 2/1989 | Leibovich et al. | 424/423 |
| 4,847,074 | 7/1989 | Hatae et al. | 424/62 |
| 4,990,330 | 2/1991 | Oyama | 424/62 |
| 5,171,845 | 12/1992 | Spik et al. | |
| 5,192,743 | 3/1993 | Hsu et al. | 514/8 |
| 5,316,767 | 5/1994 | Hara et al. | 424/63 |

FOREIGN PATENT DOCUMENTS

| | | |
|---|---|---|
| 0418704A1 | 9/1990 | European Pat. Off. |
| 53-018739 | 2/1978 | Japan . |
| 62-502544 | 10/1987 | Japan . |
| 4-210618 | 7/1992 | Japan . |
| 4210618 | 7/1992 | Japan . |
| 2052973 | 2/1981 | United Kingdom . |

OTHER PUBLICATIONS

Angiogenesis: Key Principles, eds. R. Steiner et al., 1992, pp. 235–238.

Dermatologic Clinics, vol. 6, No. 2, Apr. 1988, "Circumscribed Dermal Melanoses–Classification and Historic Features", Y. Hori, M.D., Ph.D., et al.

Biochemistry, 1988, American Chemical Society, pp. 6282–6287, "Isolation of Bovine Agiogenin using a Placental Ribonuclease Inhibitor Binding Assay" M.D. Bond, et al.

Biochemistry, 1985, American Chemical Society, pp. 5486–5494, "Amino Acid Sequence of Human Tumor Derived Angiogenin", D. J. Strydom, et al.

Biochemistry 1985, American Chemical Society, pp. 5480–5486, "Isolation and Characterization of Angiogenin, an Angiogenic Protein from Human Carcinoma Cells", J.W. Fett, et al.

Analytical Biochemistry 173, (1988); "An In Vitro Binding Assay For Angiogenin Using Placental Ribonuclease Inhibitor"; Michael D. Bond.

*Primary Examiner*—Thurman K. Page
*Assistant Examiner*—Murthy Sikha
*Attorney, Agent, or Firm*—Townsend & Banta

[57] ABSTRACT

A whitening cosmetic preparation containing angiogenin as an effective component is disclosed. Angiogenin used in the present invention may be derived from milk, especially bovine milk. The whitening cosmetic preparation contains at least 0.001% by weight, preferably from 0.01 to 20% by weight angiogenin based on the total amount of said preparation. A method for whitening skin comprising administration of angiogenin to skin is also disclosed. The whitening cosmetic preparation inhibits melanin production and prevents the developments of blotches and freckles of skin.

10 Claims, No Drawings

WHITENING COSMETIC PREPARATION AND METHOD OF USING SAME

BACKGROUND OF THE INVENTION

1. Field of the Invention

The present invention relates to a whitening cosmetic preparation containing angiogenin known to be an anglogenesis factor, as an effective component.

2. Prior Art

Angiogenin is known as a material involved in the proliferation of human tumor and the like. Angiogenin is one of several angiogenesis factors. Human angiogenin was isolated from human tumor cells by Fett et al. (J. W. Fett et al., Biochem., vol.24, 5480–5486,1985). Human angiogenin is known to be a protein of molecular weight of 14,400. Subsequently complete amino acid sequence of angiogenin has been determined by Strydom et al. (D. J. Strydom et al., Biochem., vol.24, 5486–5494,1985).

Angiogenin exists in blood and even in milk. Bond et al. have isolated bovine angiogenin from bovine blood (M. D. Bond et al., Biochem. vol. 27, 6282–6287,1988). Maes et al. have isolated angiogenin from bovine milk (P. Maes et al., FEBS LETTERS vol.241, 41–45,1988) and have determined the amino acid sequence of the angiogenin.

Japanese Patent Application (OPI) (the term "OPI" as used herein means an unexamined published patent application) No. Hei 2-296000 describes a method for recovering angiogenin by adsorbing angiogenin from milk to a cation exchange chromatography, and eluating it with an aqueous solution of an alkaline metal salt of weak organic acid and recovering the eluate by a cation exchange chromatography again and gel permeation chromatography. Angiogenin thus obtained has been researched on its physiological activities.

The most important physiological activity of angiogenin is angiogenic activity as described above. Owing to this function, usages of angiogenin for the treatments of injuries, ulcers, organ implantation, circulatory hypofunction have been suggested. However, another functions other than such function have not been known. Japanese Patent Application (OPI) No.Hei 4-210618 describes an example of the usage of angiogenin as a hair growth agent.

On the other hand, blotches and freckles and the like are resulted from melanin production in tissues due to suntan and the like. It is known that melanin may be formed by oxidizing tyrosine catalytically by tyrosinase first and then carrying out several stages of reactions. It has been proved that the development of blotches and freckles may be controlled by inhibiting the tyrosinase. Until now existences of such inhibitory effects in albutin, kojic acid and hydrogenated casein have been confirmed and thus they have been used as skin whitening agents. A variety of materials which may be used as such a skin whitening agent have been still under investigation.

SUMMARY OF THE INVENTION

An object of the present invention is to provide a skin whitening cosmetic preparation containing angiogenin as an effective component.

Another object of the present invention is to provide a skin whitening cosmetic preparation containing angiogenin derived from milk.

Another object of the present invention is to provide a method for whitening skin comprising administration of angiogenin to skin.

The inventors have researched on the physiological activities of angiogenin, and have first found that the angiogenin may control specifically melanin production of B-16 cells being melanoma cells. The above objects of the present invention can be achieved by the present invention based on these findings.

Thus the present invention provides a whitening cosmetic preparation containing angiogenin as an effective component.

The present invention also provides a method for whitening skin comprising administration of angiogenin to skin.

DETAILED DESCRIPTION OF THE PRESENT INVENTION

The present invention will be described in detail hereinafter.

Angiogenin used as a raw material of the present invention may be derived from any origin or from any species. For example, gene sequences of angiogenin derived from human and bovine, have been determined and thus angiogenin may be made by a method using genetic recombination. Accordingly, angiogenin produced by the genetic recombination may be used in the present invention. Further, angiogenin is contained in bovine colostrum in a relatively high amount as described above so that angiogenin recovered from milk may be used in the present invention. In addition, angiogenin may be recovered from a culture liquid of cell culture. Japanese Patent Application (OPI) No.62-502544 describes an example of angiogenin recovered from cell culture liquid. In the present invention such kinds of angiogenin may be used.

A method for preparing a skin whitening cosmetic preparation using angiogenin extracted from mammals milk and a whitening cosmetic preparation prepared by the method will be described. However, angiogenin used in the present invention should not be limited by angiogenin derived from milk.

An example of a method for obtaining angiogenin from milk will be described hereinafter.

As milk containing angiogenin, colostrum collected from human, bovine, sheep, goat and the like within one to seven days after delivery, especially one to five days after delivery are appropriate since the content of angiogenin fraction is high. However, milk collected from another mammals or normal lactation milk may be used as a raw material in the present invention. In the present invention, these milks may be degreased first, then the milks may be made to contact with sulfated polysaccharide having a function of adsorbing lactoferrin and lactoperoxidase(LPO) selectively so that lactoferrin and LPO may be made to be adsorbed to the sulfated polysaccharide. At this point, angiogenin is adsorbed simultaneously.

The sulfated polysaccharide may include sulfonated arginate, sulfonated cellulose, sulfonated dextran, sulfonated chitosan as preferable examples. Sulfonated chitosan is most preferable in the present invention. The sulfonated chitosan is on the market under the name of sulfonated Chitopearl by Fuji Boseki Co., Ltd. and thus is easily available. The amount of sulfon groups introduced into the sulfonated Chitopearl is preferably controlled to 10 to 50 µeq/1 ml carrier, more preferably controlled to 27 to 40 µeq/1 ml carrier.

The adsorption procedures may be conducted using carrier gel of about 0.5 to 5% by volume of the degreased milk volume. The adsorption procedures may be performed by adopting various methods such as batch process and a method in which degreased colostrum is run through a column which has been filled with carrier. However, the circulating method using the rotary type column described in Japanese Patent Application(OPI) No.Hei 3-109400 has high adsorption rates and thus is preferable.

The carrier may be then washed with an aqueous solution or buffer solution having an ionic strength of equal or less than 0.2 and pH of equal or less than 5 to wash out impurities stopped within the carrier. After washing, the carrier was eluted with an aqueous solution or a buffer solution having an ionic strength of equal or more than 0.5 and pH of equal or more than 5, preferably having an ionic strength of 0.7 to 2.0 and pH of 6 to 8 in order to eluate the adsorption fraction.

The fraction may be desalted since the fraction contains the salts used in the eluation procedures. The desalting procedures may be conducted by a method for desalting by dialysis, ion exchange, molecular sieves and the like. Desairing, concentration and purification of angiogenin-containing fraction may be carried out at the same time by adopting a step in which a fraction having a molecular weight of equal or less than 50 kD is removed by an ultrafiltration membrane. The desalting effects of the ultrafiltration may be decided by making electrical conductivity and sulfate ion concentration to serve as indications. When electrical conductivity is 400 μs/cm and the sulfate ion concentration is equal or less than 0.294% (per total solids content), the ultrafiltration may be completed.

By the above procedures, the angiogenin-containing fraction may be recovered. The fraction may be powdered by drying. However, it is preferable to carry out drying under a condition of a temperature as low as possible, for example freeze-drying, in order to prevent deactivation.

The fraction thus obtained may be dissolved in a small amount of Tris-HCl buffer solution (pH 7.0) containing 1 to 5M, preferably 2 to 3M sodium thiocyanate. Sodium thiocyanate is essential matter to dissolve angiogenin being an effective component of the present invention. The dissolved samples may be subjected to a centrifugation or filtration procedure to remove the impurities, and then may be added by cooled ethanol so that the final concentration is reduced to 50 to 80%. After leaving the solution to stand for one hour at −40° C., or for one day and night at equal or less than 5° C., the formed precipitates may be removed. Lactoferrln and LPO which behave together with angiogenin are transferred to ethanol precipitates phase, and angiogenin remains in ethanol phase. After concentration, the angiogenin-containing supernatant may be desalted such as by dialysis to recover a fraction containing a high amount of angiogenin. The fraction may be freeze-dried, if necessary. The confirmation that the recovered fraction is angiogenin may be made by determining the inhibitory activity against ribonuclease inhibitor using the method described by Bond et al. (M. D. Bond et al., Analytical Biochemistry, vol.173, 166–173,1988).

Further, N-terminal amino acid sequence of the fraction obtained may be analyzed using an amino acid sequencer so as to confirm the fraction by the amino acid sequence, if necessary.

The whitening cosmetic preparation of the present invention contains angiogenin having a concentration of at least 0.001% by weight, preferably 0.01 to 20% by weight. The skin whitening cosmetic preparation may be produced in an appropriate forms such as cream, emulsion, cosmetic lotion and the like by a conventional method using cosmetic base materials which have been conventionally used. The whitening cosmetic preparations may contain a known optional additives such as UV absorbing agent, UV scattering agent, melanin. synthesis inhibitor such as albutin, and another pharmaceutically effective components, thickening agent, plasticizer, colorant, flavor and the like. Further, angiogenin has been proved to be neither toxic nor stimulating to skin and to have no side effect.

As described above, an skin whitening cosmetic preparation containing angiogenin is provided by the present invention. The whitening cosmetic preparation has proved to be safe since it does not have influence upon the cell growth even on the test using cells and to have high whitening effect.

EMBODIMENT

The present invention will be described in detail by reference to the following non-limiting examples.

EXAMPLE 1

Recovery of Angiogenin from Bovine Degreased Milk (1) Raw bovin milk extracted and collected from normal heifers was subjected to centrifugation to have degreased milk, i.e. skim milk. 200 L of the degreased milk (cooled to 14° C.). was run through a rotary type of absorption device (manufactured by Tokyo Rika Co., Ltd.) having internal space of 1474 ml filled with 882 ml sulfonated Chitopearl SU-3 (manufactured by Fuji Boseki Co., Ltd.) in which the amount of sulfonic groups introduced was 38.9 μeq/ml gel. The running rate was 25 kg/hour and the running was repeated twice time. The revolution number of the rotary type of reactor was controlled to 30 rpm.

(2) Then 40 L hot water at 30° to 35° C. was running through as described in the above step (1) to perform washing. The washing was confirmed by measuring absorbance at 280 nm using a cell having a light path length of 1 cm. When absorbance is equal or less than 0.01, washing was completed.

(3) After washing, eluation was performed by running through about 67.5 L of 0.7M saline solution (prepared by dissolving in 0.5 mM of sodium bicarbonate, pH 7.0). The eluation was confirmed when absorbance at 280 nm was measured using a cell having a light path length of 1 cm to be in the range from 0.015 to 0.020. 66.5 kg eluate was recovered. The electrical conductivity of the recovered solution was 26.5 ms/cm.

(4) The solution obtained in the above step (3) was ultrafiltered to make concentration using a ultrafiltration device set with a UF membrane of 50 kD. The electrical conductivity and the concentration of sulfate ions were determined. The concentration procedures were completed at the time when the electrical conductivity was 400 μS/cm and the concentration of sulfate ions was 0.29% (per total solids content) to recover a fraction containing angiogenin. The fraction was then freeze-dried to obtain 9.11 g dried powder.

(5) 720 mg fraction containing angiogenin obtained in the above step(4) was dissolved in 100 ml of 10 mM Tris-HCl buffer solution (pH 7.0) containing 3M sodium thiocyanate. After dissolving, the solution was centrifuged for 30 minutes at 1,000 r.p.m. so as to remove insoluble materials.

(6) Then to the supernatant, cooled ethanol was added so as to have ethanol concentration of 80%. The mixture was left to stand at about −40°C. for one hour and then centrifuged to remove the precipitates.

(7) After removing the precipitates, the supernatant was transferred to an rotary evaporator to concentrate until the liquid amount was reduced to 80 ml. The concentrated liquid was then transferred to an dialysis tube, and dialysis was performed against distilled water for one night, and freeze-dried. Thus about 9 mg angiogenin was recovered.

EXAMPLE 2

Recovery of Angiogenin from Bovine Colostrum

Bovine milk collected from cows within 5 days after delivery was centrifuged to have 100 L degreased milk. The subsequent procedures were performed as described in Example 1 to obtain 200 mg angiogenin.

EXAMPLE 3

Examples of formulations of cosmetic preparations having skin whitening effect will be shown hereinafter.

(1) Cosmetic Lotion (oily type)

| | |
|---|---|
| Sorbitol (70%) | 3.0 g |
| Glycerin | 5.0 g |
| Angiogenin | 0.2 g |
| Water | 70.0 g |

To the mixed solution containing the above components, a mixed solution containing

| | |
|---|---|
| Allantoin | 0.1 g |
| Polyoxyethylene hardened castor oil derivative | 0.5 g |
| Ethanol | 20.0 g and |
| Flavor | proper quantity | was added with stirring to make a uniform solution to obtain a cosmetic lotion having skin whitening effect.

(2) Cosmetic Lotion (dry type)

| | |
|---|---|
| Ethylene Glycol | 2.5 g |
| Propylene Glycol | 5.0 g |
| Silicone | 0.0001 g |
| Angiogenin | 0.05 g |
| Water | 70.0 g |

To the mixed solution containing the above components, a mixed solution containing

| | |
|---|---|
| Urea | 1.0 g |
| Polyoxyethylene sorbitan monolaurate | 1.2 g |
| Ethanol | 20.0 g |
| ε-amino caproic acid | 0.1 g and |
| Flavor | proper quantity | was added with stirring to make a uniform solution to obtain a cosmetic lotion having a skin whitening effect.

(3) Face Washing Cream

| | |
|---|---|
| Glycerin | 2.0 g |
| Stearic acid | 20.0 g |
| Myristic acid | 10.0 g |
| Lauric acid | 5.0 g |
| Polyoxyethylene laurylether | 1.0 g |

-continued

| | |
|---|---|
| Angiogenin | 0.1 g |
| Flavor and Preservative | proper quantity |

The above components were mixed and heated at 75° C. to dissolve them, and the mixed solution containing

| | |
|---|---|
| Potassium hydroxide | 5.5 g and |
| Water | 56.0 g | was added with stirring and cooled to obtain face washing cream having a skin whitening effect.

(4) Oily Cream

| | |
|---|---|
| Beeswax | 10.0 g |
| Paraffin wax | 6.0 g |
| Lanolin | 3.0 g |
| Isopropyl myristate | 6.0 g |
| Squalane | 8.0 g |
| Liquid paraffin | 25.0 g |
| Angiogenin | 0.5 g |
| Polyoxyethylene sorbitan monostearate | 1.8 g |
| Sorbitan monostearate | 4.2 g |
| Preservative | proper quantity |

These components were mixed and heated at 75° C. to dissolve them, and the mixed solution containing

| | |
|---|---|
| Propylene glycol | 2.0 g |
| Boron | 0.7 g |
| Urea | 5.0 g and |
| Water | 28.0 g | was added with stirring, cooled, and added by flavor to obtain an oily cream having a skin whitening effect.

REFERENCE EXAMPLE

In the reference example, the inhibitory activity of melanin production by angiogenin derived from milk obtained in Example 1 will be explained.

(1) Biological Activity Measurement

Mouse melanoma B16 cells seeded a culture plate having 24 wells at a density of $1\times10^5$/ml/well and the cells were incubated for 24 hours under a culture condition of 37° C. and 5% CO. Then 1 ml each of angiogenin solution so prepared using Dulbecco Modified Eagle Medium(DMEM) containing 10% fetal bovine serum(FCS) as to have a concentration of 5 μg/ml per well and of angiogenin solution diluted twice by step dilution with DMEM by using the above solution as a stock solution were added to each well. In addition, albutin which was known to inhibit the melanin production of melanoma cells and to have skin whitening effect was so prepared with DMEM as to have a final concentration of 50 μM and 1 ml of the prepared albutin was added in the same manner as a positive control. Then the culture plate was further incubated for six days under a culture condition of 37° C. and 5% $CO_2$. After six days, absorbances at 490 nm of the well added by various concentrations of angiogenin and of the well added by albutin were measured, with the well added by only DMEM being used as control. The inhibitory activities of melanin productions of each well were calculated by the following equation:

Inhibitory rate(%)={1-(absorbance of sample/absorbance of control)}×100

(2) Inhibitory Activity of Melanin Production

The inhibitory activities of melanin productions of melanoma cells in each well containing various concentrations of angiogenin and albutin will be shown in Table 1.

TABLE 1

| Sample (conc. per well) | Inhibition Rate (%) |
|---|---|
| Angiogenin(5 μg/ml) | 41.4 |
| (x1/2) | 59.4 |
| (x1/4) | 56.8 |
| (x1/8) | 41.6 |
| (x1/16) | 43.8 |
| (x1/32) | 7.7 |
| Albutin(50 μM) | 28.2 |

The angiogenin showed the strong inhibitory effect on melanin production even at a concentration of about 0.15 μg/ml.

While particular forms of the present invention have been described, it will be apparent that various modifications can be made without departing from the spirit and scope of the invention. Accordingly, it is not intended that the invention be limited except as by the appended claims.

We claim:

1. A method of inhibiting melanin production to whiten facial skin, comprising the step of applying to facial skin a cosmetic whitening composition having an effective amount of angiogenin for inhibiting melanin production and a cosmetically acceptable component for facial skin.

2. A method of inhibiting melanin production to whiten facial skin comprising the step of applying to facial skin a cosmetic whitening composition comprising angiogenin at a concentration of at least 0.001% by weight for inhibiting melanin production and a cosmetically acceptable component.

3. A method for inhibiting melanin production to whiten facial skin according to claim 2, wherein said composition contains angiogenin at a concentration of from about 0.01 to 20% by weight.

4. The method of claim 2, wherein the whitening composition is applied directly to facial skin.

5. The method of claim 2, wherein the cosmetically acceptable component is selected from the group consisting of creams, emulsions and lotions for facial skin.

6. The method of claim 2, wherein the whitening composition comprises one or more additives selected from the group consisting of UV-absorbing agents U.V. scattering agents, thickening agents, plasticizer, colorant and flavor.

7. The method of claim 2, wherein the angiogenin is derived from milk.

8. The method of claim 2, wherein the angiogenin is derived from colostrum.

9. A method of inhibiting melanin production to whiten facial skin comprising the step of applying to facial skin an effective amount of angiogenin for inhibiting melanin production and a cosmetically acceptable carrier for facial skin.

10. A method of inhibiting melanin production to whiten facial skin comprising the step of applying to facial skin an effective amount of angiogenin for inhibiting melanin production.

* * * * *